(12) United States Patent
Bloom et al.

(10) Patent No.: US 7,408,078 B2
(45) Date of Patent: Aug. 5, 2008

(54) ANTHRANILIC ACID DERIVATIVES USEFUL IN TREATING INFECTION WITH HEPATITIS C VIRUS

(75) Inventors: Jonathan D. Bloom, Nyack, NY (US); Thomas R. Bailey, Phoeniville, PA (US)

(73) Assignees: Wyeth, Madison, NJ (US); ViroPharma Incorporated, Exton, PA (US)

( * ) Notice: Subject to any disclaimer, the term of this patent is extended or adjusted under 35 U.S.C. 154(b) by 328 days.

(21) Appl. No.: 10/682,647

(22) Filed: Oct. 8, 2003

(65) Prior Publication Data

US 2005/0004192 A1    Jan. 6, 2005

Related U.S. Application Data

(60) Provisional application No. 60/416,521, filed on Oct. 8, 2002.

(51) Int. Cl.
*C07C 229/34*    (2006.01)
(52) U.S. Cl. .................... 562/456; 562/433; 562/457; 562/458; 560/19; 560/43; 560/47; 560/48
(58) Field of Classification Search .................. None
See application file for complete search history.

(56) References Cited

U.S. PATENT DOCUMENTS 5,637,597 A * 6/1997 Matsuda et al. ............. 514/312
5,741,926 A    4/1998 Bierer et al. ................. 562/457
6,218,437 B1    4/2001 Chojkier ..................... 514/731
6,383,768 B1    5/2002 De Francesco et al. ........ 435/15

FOREIGN PATENT DOCUMENTS

EP        1 230 260        8/2000
WO        WO 02/08187    1/2002

OTHER PUBLICATIONS

Wright et al. J. Med. Chem. 2001, 44, 3187-3194.*
Ryznerski et al. Acta. Polon. Pharm. XXXVIII, 1981, 5, p. 534-537.*
Hepatology, vol. 26 (Suppl. 1), 1997 pp. 2S-10S.
Hepatology, vol. 26 (Suppl. 1), 1997 pp. 11S-14S.
Antiviral Chemistry and Chemotherapy, vol. 8, 1997, pp. 281-301.
J. General Virology, vol. 81, 2000, pp. 1631-1645.
Ryznerski et, al., "Phenoxyacetamide Derivatives With Potential Antiinflammatory Activity", Chem. Abs. , 1982:455420.
Ryznerski et, al., "Synethesis and Antiinflammatory Properties of N-(2- Carboxyphenyl) phenoxyacetamides", Chem. Abs., 1980:567828.

* cited by examiner

*Primary Examiner*—Yvonne Eyler
*Assistant Examiner*—Yevegeny Valenrod
(74) *Attorney, Agent, or Firm*—Fitzpatrick, Cella, Harper & Scinto

(57) ABSTRACT

The present invention provides pharmaceutical compositions useful in treating hepatitis C infection. The present invention also provides methods of treating hepatitis C infection by administering to a mammal the pharmaceutical compositions of the present invention.

12 Claims, No Drawings

ANTHRANILIC ACID DERIVATIVES USEFUL IN TREATING INFECTION WITH HEPATITIS C VIRUS

This application claims the benefit of U.S. Provisional Patent Application No. 60/416,521, filed Oct. 8, 2002, the disclosure of which is incorporated by reference herein in its entirety.

BACKGROUND OF THE INVENTION

1. Field of the Invention

This invention relates to a series of anthranilic acid compounds that are useful in the treatment of hepatitis C infection.

2. Related Background Art

Hepatitis C is a common infection that can lead to chronic hepatitis, cirrhosis, liver failure, and hepatocellular carcinoma. Infection with the hepatitis C virus (HCV) leads to chronic hepatitis in at least 85% of cases. It is the leading reason for liver transplantation, and is responsible for at least 10,000 deaths annually in the United States (Hepatology, 1997, 26 (Suppl. 1), 2S-10S).

The hepatitis C virus is a member of the Flaviviridae family. The genome of HCV is a positive strand, single-stranded linear (Hepatology, 1997, 26 (Suppl. 1), 11S-14S). HCV displays extensive genetic heterogeneity; at least six genotypes and more than 50 subtypes have been identified.

There is currently no effective vaccine to prevent HCV infection. The only therapy currently available is treatment with interferon-α (INF-α or combination therapy of INF-α with the nucleoside analog ribavirin (Antiviral Chemistry and Chemotherapy, 1997, 8, 281-301). However, only about 40% of treated patients develop a sustained response. Thus, there remains a need for more effective anti-HCV therapeutic agents.

Following infection by HCV, the viral RNA is translated into a polyprotein. This approximately 3,000 residue polyprotein is subsequently cleaved into individual proteins by host peptidases, as well as virally encoded proteases. The HCV genome encodes at least 10 structural (required for viral assembly) and nonstructural proteins (required for replication). Some of the nonstructural proteins include: NS2, NS3, NS4A, NS4B, NS5A, and NS5B (J. General Virology, 2000, 81, 1631-1648). NS5B is a RNA dependent RNA polymerase that is essential for viral replication. In positive stranded RNA viruses, such as HCV, RNA is the sole genetic material. Since mammal host cells ordinarily lack RNA-dependent RNA polymerase activity, the positive stranded RNA viruses encode their own replicative polymerase (NS5B in the case of HCV), which is essential for the production of virion progeny. The inhibition of NS5B activity, therefore, provides choice target for HCV drug design.

SUMMARY OF THE INVENTION

This invention relates to the use of a series of anthranilic acid derivatives for the treatment of hepatitis C by virtue of their ability to inhibit hepatitis C polymerase (NS5B).

In accordance with this invention there is provided a group of compounds represented by formulae (I) and (II):

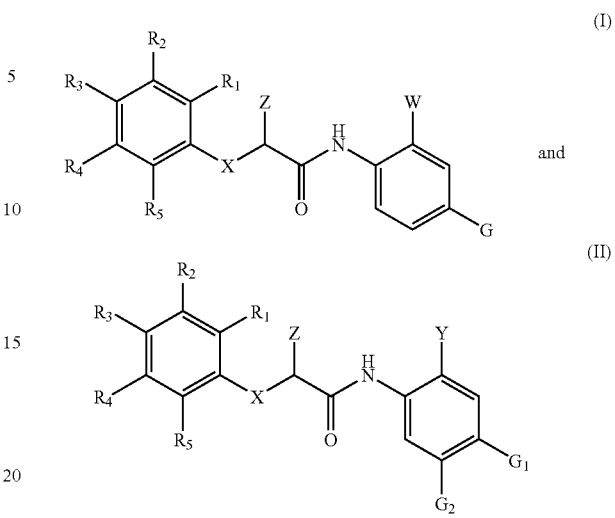

and pharmaceutically acceptable salts thereof, wherein:

$R_1$, $R_2$, $R_3$, $R_4$ and $R_5$ are independently selected from the group consisting of hydrogen, halogen, methyl, ethyl, methoxy, nitro, $C_2$-$C_4$ alkenyl, cyano, and trifluoromethyl;

X is O, S, NH, or NR where R is a $C_1$-$C_4$ alkyl group;

W is $CO_2H$ or 5-tertrazolyl;

Y is $CO_2H$ or $CO_2CH_3$;

Z is hydrogen or mono-methyl;

G is either OH, F, or hydrogen;

$G_1$ is OH, F, methoxy or hydrogen; and $G_2$ is either OH, Cl, methoxy or hydrogen.

Preferred compounds of formulae I and II useful as agents for the treatment of HCV include:

2-{[(2,4-dichlorophenoxy)acetyl]amino}benzoic acid,
2-{[(2,5-dimethylphenoxy)acetyl]amino}benzoic acid,
2-{[(2-ethoxy-5-Z-(2-propenyl)phenoxy)acetyl]amino}benzoic acid,
2-{[(2-bromo-5-fluorophenoxy)acetyl]amino}benzoic acid,
2-{[(2-methyl-5-nitrophenoxy)acetyl]amino}benzoic acid,
2-{[(2-fluoro-5-methylphenoxy)acetyl]amino}benzoic acid,
2-[2-(4-Bromo-phenoxy)-acetylamino]-benzoic acid,
2-[2-(3-Bromo-phenoxy)-acetylamino]-benzoic acid,
2-[2-(2-Bromo-phenoxy)-acetylamino]-benzoic acid,
2-[2-(4-Bromo-phenoxy)-propionylamino]-benzoic acid,
2-[2-(4-Bromo-phenylsulfanyl)-acetylamino]-benzoic acid,
2-[2-(4-Chloro-phenoxy)-acetylamino]-benzoic acid,
2-[2-(4-Fluoro-phenoxy)-acetylamino]-benzoic acid,
2-{[(3-chlorophenoxy)acetyl]amino}benzoic acid,
2-{[(3-chlorophenoxy)acetyl]amino}-5-fluorobenzoic acid,
2-{[(3-chlorophenoxy)acetyl]amino}-5-hydroxybenzoic acid,
2-{[(3,4-dimethylphenoxy,acetyl]amino}-5-hydroxybenzoic acid,
2-{[(3-bromophenoxy)acetyl]amino}-5-hydroxybenzoic acid,
2-{[(2S)-2-(4-chlorophenoxy)propanoyl]amino}benzoic acid, 2-{[(2,3-dichlorophenoxy)acetyl]amino}-5-hydroxybenzoic acid,
2-{[(2,4,5-trichlorophenoxy)acetyl]amino}benzoic acid,
2-{[(2,4-dibromophenoxy)acetyl]amino}benzoic acid,
2-{[(2-chlorophenoxy)acetyl]amino}benzoic acid,
2-{[N-(3-bromophenyl)glycyl]amino}benzoic acid,
2-{[N-(4-bromo-3-chlorophenyl)-N-methylglycyl]amino}benzoic acid,
2-{[(4-chloro-2-methylphenoxy)acetyl]amino}benzoic acid,
2-{[(5-chloro-2-methylphenoxy)acetyl]amino}benzoic acid
2-{[(3,4-difluorophenoxy)acetyl]amino}benzoic acid,
2-(4-chlorophenoxy)-N-[2-(1H-tetrazol-5-yl)phenyl]acetamide,
2-{[N-(3,4-dibromophenyl)-N-methylglycyl]amino}benzoic acid,
2-{[N-(2,5-dibromophenyl)glycyl]amino}benzoic acid,
2-{[(2-cyanophenoxy)acetyl]amino}benzoic acid,
5-hydroxy-2-{[(2,4,5-trichlorophenoxy)acetyl]amino}benzoic acid,
2-{[(2-chloro-4,5-dimethylphenoxy)acetyl]amino}benzoic acid,
2-({[4-chloro-3-(trifluoromethyl)phenoxy]acetyl}amino)benzoic acid,
2-{[(2-bromo-4-chloro-5-methylphenoxy)acetyl]amino}benzoic acid,
2-{[(2-ethyl-4,5-dimethylphenoxy)acetyl]amino}benzoic acid,
2-({[(3,4-dichlorophenyl)sulfanyl]acetyl}amino)benzoic acid,
2-({[(4-chlorophenyl)sulfanyl]acetyl}amino)benzoic acid,
2-{[(2-bromo-4,5-difluorophenoxy)acetyl]amino}benzoic acid,
2-({[3-(trifluoromethyl)phenoxy]acetyl}amino)benzoic acid,
2-{[(2-bromo-4-chloro-5-methylphenoxy)acetyl]amino}-5-hydroxybenzoic acid,
2-{[(2,4,5-trifluorophenoxy)acetyl]amino}benzoic acid,
2-{[(3,5-dichlorophenoxy)acetyl]amino}-5-hydroxybenzoic acid,
2-({[(2,4,5-trichlorophenyl)thio]acetyl}amino)benzoic acid,
2-{[N-(3,4-dichlorophenyl)-N-methylglycyl]amino}benzoic acid,
2-{[(3,5-difluorophenoxy)acetyl]amino}benzoic acid,
2-{[(3,5-difluorophenoxy)acetyl]amino)-5-hydroxybenzoic acid,
2-{[(2-bromophenoxy)acetyl]amino)-5-hydroxybenzoic acid,
2-{[(2-chloro-6-methylphenoxy)acetyl]amino}benzoic acid,
2-{[(4-chloro-3-ethylphenoxy)acetyl]amino}benzoic acid,
2-{[N-(2,4,5-trichlorophenyl)glycyl]amino}benzoic acid,
5-hydroxy-2-{[N-(2,4,5-tichlorophenyl)glycyl]amino}benzoic acid,
2-{[(3-chloro-4-methylphenoxy)acetyl]amino}benzoic acid,
2-{[(3-chloro-4-methylphenoxy)acetyl]amino}-5-hydroxybenzoic acid,
2-{[(2-chloro-5-fluorophenoxy)acetyl]amino}benzoic acid,
2-{[(2-chloro-5-fluorophenoxy)acetyl]amino}-5-hydroxybenzoic acid,
2-{[(3-chloro-4-fluorophenoxy)acetyl]amino}benzoic acid,
2-{[(3-chloro-4-fluorophenoxy)acetyl]amino}-5-hydroxybenzoic acid,
2-{[(4-chloro-3-fluorophenoxy)acetyl]amino}benzoic acid,
2-{[N-(3,4-difluorophenyl)glycyl]amino}benzoic acid,
2-{[N-(3,4-dichlorophenyl)glycyl]amino}benzoic acid,
2-{[N-(2,5-dibromophenyl)glycyl]amino}-5-hydroxybenzoic acid,
2-{[N-(4-chloro-2-fluorophenyl)glycyl]amino}benzoic acid,
2-{[(4-chloro-3-fluorophenoxy)acetyl]amino}-5-hydroxybenzoic acid,
2-{[N-(2-fluoro-4-methylphenyl)glycyl]amino}benzoic acid,
2-{[N-(3,4-dichlorophenyl)glycyl]amino}-5-hydroxybenzoic acid,
2-{[N-(2,5-dichlorophenyl)glycyl]amino}benzoic acid,
2-{[N-(2,5-dichlorophenyl)glycyl]amino}-5-hydroxybenzoic acid,
2-{[N-(3,4-dichlorophenyl)-N-ethylglycyl]amino}benzoic acid,
2-{[N-(3,4-dichlorophenyl)-N-ethylglycyl]amino}-5-hydroxybenzoic acid,
2-{[N-(3,4-dichlorophenyl)-N-propylglycyl]amino}benzoic acid,
2-{[N-(3,4-dichlorophenyl)-N-propylglycyl]amino}-5-hydroxybenzoic acid,
2-{[N-(2,5-dichlorophenyl)-N-methylglycyl]amino}-5-hydroxybenzoic acid,
2-{[N-(3,4-dichlorophenyl)-N-methylglycyl]amino}-5-hydroxybenzoic acid, and
2-{[N-(3-chloro-4-fluorophenyl)glycyl]amino}benzoic acid,
2-{[(3,4,-dimethylphenoxy)acetyl]amino}-5-hydroxybenzoic acid,
2-{[(3,4,-dimethylphenoxy)acetyl]amino}-4-hydroxybenzoic acid,
2-{[(2-chlorophenoxy)acetyl]amino}-5-hydroxybenzoic acid,
2-{[(2-bromo-4-methylphenoxy)acetyl]amino}benzoic acid,
2-{[(4-nitrophenoxy)acetyl]amino}-5-hydroxybenzoic acid,
2-{[2-(2-chloro-phenoxy)acetyl]amino}benzoic acid,
2-[(2-phenoxy)propionylamino]-4-hydroxybenzoic acid,
2-[{(4-bromophenyl)methyl}{2-isopropyl-5-methylphenoxyacetyl}amino]benzoic acid,
2-{[(4-cyclohexylphenoxy)acetyl]amino}benzoic acid,
2-[(4-chlorophenoxy)acetylamino]-benzoic acid methyl ester,
2-[(4-methoxyphenoxy)acetylamino]-benzoic acid methyl ester,
2-[(4-cyclohexylphenoxy)acetylamino]-4,5-dimethoxybenzoic acid,
2-[(3-methylphenoxy)acetylamino]-4,5-dimethoxybenzoic acid,
2-[(3-methylphenoxy)acetylamino]-4-chlorobenzoic acid; and pharmaceutically acceptable salts thereof More preferred compounds include:
2-{[(2,4,5-trichlorophenoxy)acetyl]amino}benzoic acid,
2-{[N-(2,5-dibromophenyl)glycyl]amino}-5-hydroxybenzoic acid,
2-{[N-(3,4-dichlorophenyl)glycyl]amino}-5-hydroxybenzoic acid, and pharmaceutically acceptable salts thereof.

Most preferred compounds include:
5-hydroxy-2-{[(2,4,5-trichlorophenoxy)acetyl] amino}benzoic acid,
2-{[(2-bromo-4-chloro-5-methylphenoxy)acetyl]amino}-5-hydroxybenzoic acid,
2-{[N-(3,4-dichlorophenyl)-N-methylglycyl]amino}-5-hydroxybenzoic acid, and pharmaceutically acceptable salts thereof.

In one embodiment of the present invention, there is provided pharmaceutical compositions for the treatment of hepatitis comprising at least one of the above described compounds.

The present invention also provides a method of treating hepatitis C in a mammal, including humans. This method comprises administering to a mammal an effective amount of the above described pharmaceutical compositions.

DETAILED DESCRIPTION OF THE INVENTION

As discussed above, the HCV virus is a positive strand RNA virus. Thus the replication of HCV proceeds via an initial synthesis of a complementary negative RNA strand. This negative RNA strand serves as a template for the production of progeny positive strand RNA molecules. The initial synthesis of the complementary negative RNA strand is brought about by the hepatitis C virus's own RNA-dependent RNA polymerase, NS5B. Thus, inhibition of the NS5B polymerase represents a viable target in the treatment against infection of HCV.

Compounds of the present invention inhibit the hepatitis C RNA-dependent RNA polymerase, NS5B. Since the compounds of the present invention inhibit NS5B activity, and therefore inhibit the ability of the virus to produce a negative strand RNA to serve as a template for progeny RNA, pharmaceutical compositions comprising these compounds, either alone or in combination with each other, offer a treatment against hepatitis C infection. The present invention accordingly provides a pharmaceutical composition that comprises a compound of this invention in combination or association with a pharmaceutically acceptable carrier.

The compounds of the present invention can be prepared by methods known to those skilled in the art or by the synthetic methods disclosed in U.S. Pat. No. 5,741,926 (Bierer and Dubenko). A preferred method is illustrated below in scheme 1:

Scheme 1

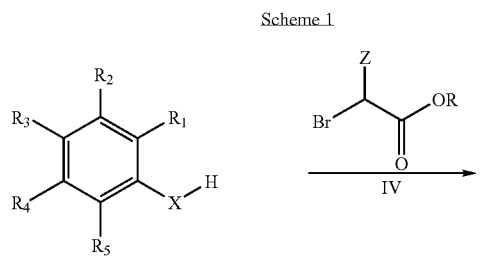

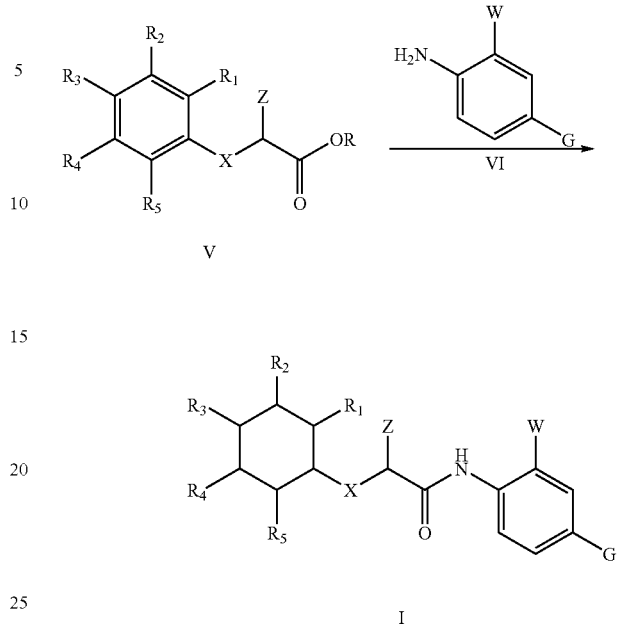

A phenol or aniline (III) is alkylated with a bromoacetic acid derivative (IV) to form intermediate V. Activation of the carboxy group by standard methods and coupling to aniline VI yields the product of formula I, wherein $R_1$, $R_2$, $R_3$, $R_4$ and $R_5$ are independently selected from the group consisting of hydrogen, halogen, methyl, ethyl, methoxy, nitro, $C_2$-$C_4$ alkenyl, cyano, and trifluoromethyl; X is O, S, NH, or NR where R is a $C_1$-$C_4$ alkyl group; W is $CO_2H$ or 5-tertrazolyl; Z is hydrogen or mono-methyl and G is either OH, F, or hydrogen. Compounds of formula II can be prepared in a similar manner.

The phrase pharmaceutically acceptable salts is well understood by those of ordinary skill in the art and may include, for example, those salts derived from such organic and inorganic acids such as acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, tolunesulfonic, salicycic, benzoic and simliarly known acceptable acids.

Some compounds, e.g. when Z is methyl, used in this invention may include both R and S stereoisomers. Throughout this application, for those compounds that may exist as enantiomers, the name of the compound used in this invention that does not designate absolute configuration is intended to encompass the individual R and S enantiomers as well as mixtures of the two.

The compounds of the present invention are useful in treating HCV in a mammal, including humans. When administered to a mammal the compounds can be used alone, or as a pharmaceutical composition comprising a physiologically acceptable carrier such as water, an aqueous solution, normal saline, or other physiologically acceptable excipient.

Pharmaceutical compositions comprising the compounds of the present invention can be administered by a number of routes, including, but not limited to: orally, injection including, but not limited to, intravenously, intraperitoneally, subcutaneously, intramuscularly, etc; topically, nasally; and parenterally. Additionally, the compounds can be administered in conjunction with another antiviral agent or HCV agent including IFN-α and ribavirin.

The compositions are preferably adapted for oral or subcutaneous administration. In order to obtain consistency of administration, it is preferred that the compositions of the present invention are in the form of a unit dose. Such unit dose forms may contain from 0.1 to 100 mg of a compound of the invention and preferably contain from 2 to 50 mg. Still further, preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from one to six times a day, more usually from one to four times a day. The compositions of the invention may be formulated with conventional excipients, such as a filler, a disintegrating agent, a binder, a lubricant, a flavoring agent and the like.

Pharmaceutical compositions of the present invention suitable for oral administration may be administered as discrete units such as capsules, cachets or tablets, each containing a predetermined amount of the compound(s); as a powder or granules; as a solution or a suspension in an aqueous liquid or a non-aqueous liquid; or as an oil-in-water liquid emulsion or a water-in-oil liquid emulsion and as a bolus, etc.

A tablet may be made by compression or molding, optionally with one or more accessory ingredients. Compressed tablets may be prepared by compressing in a suitable machine the aniline derivative in a free-flowing form such as a powder or granules, optionally mixed with a binder, lubricant, inert diluent, preservative, surface-active or dispersing agent known to those skilled in the art. Molded tablets may be made by molding in a suitable machine a mixture of the powdered compound moistened with an inert liquid diluent. The tablets may optionally be coated or scored and may be formulated so as to provide slow or controlled release of the aniline derivative(s) therein.

Formulations suitable for topical administration include lozenges comprising the ingredients in a flavored basis, usually sucrose and acacia or tragacanth; pastilles comprising the compound in an inert basis such as gelatin and glycerin, or sucrose and acacia; and mouthwashes comprising the compound to be administered in a suitable liquid carrier.

Pharmaceutical compositions suitable for topical administration to the skin may be administered as ointments, creams, gels, and pastes comprising the compound(s) to be administered in a pharmaceutically acceptable carrier. A preferred topical delivery system is a transdermal patch containing the compound(s) to be administered.

Pharmaceutical compositions suitable for nasal administration wherein the carrier is a solid, include a coarse powder having a particle size, for example, in the range of 20 to 500 microns, which is administered by rapid inhalation through the nasal passage from a container of the powder held close up to the nose. Suitable formulations for nasal administration wherein the carrier is a liquid, as for example a nasal spray or as nasal drops, include aqueous or oily solutions of the compounds(s).

Pharmaceutical compositions suitable for parenteral administration include aqueous and non-aqueous sterile injection solutions that may contain antioxidants, buffers, bacteriostats and solutes that render the formulation isotonic with the blood of the intended recipient; and aqueous and non-aqueous sterile suspensions that may include suspending agents and thickening agents. The formulations may be presented in unit-dose or multidose containers, for example, sealed ampules and vials, and may be stored in a freeze-dried (lyophilized) condition requiring only the addition of a sterile liquid carrier, for example water for injections, immediately prior to use. Extemporous injection solutions and suspensions may be prepared from sterile powders, granules, and tablets of the kind described above.

It should be understood that in addition to the additives particularly mentioned above, the compositions of this invention may include other agents conventional in the art having regard to the type of composition in question. For example, those suitable for oral administration may include flavoring agents.

The compounds of the present invention can be administered in an effective amount either as neutral compounds or as anionic or cationic pharmaceutically acceptable salts using counter ions such as acetate, chloride, bromide, iodide, tartrate, fumarate, succinate, ascorbate, gluconate, malate, citrate, sodium, potassium, ammonium, trialkylammonium, etc.

The present invention further provides a method of treating hepatitis C infection in mammals, including humans and/or a method of treating symptoms of hepatitis C infection. Hepatitis C infection in mammals and particularly humans often manifests itself in various clinical symptoms. These clinical symptoms or manifestations may include, but are not limited to abdominal pain, jaundice, hepatosplenomegaly, and ascites. Further, laboratory and imaging test results of a hepatitis C infection may include, but are not limited to, elevated serum aminotransferase, bilirubin, and gamma-globulin levels, as well as an enlarged liver on computed tomography, magnetic resonance imaging, and hepatic ultrasonography. Hepatic morphological and histological indicators of hepatitis C may include, but are not limited to, deposition of fibrotic tissue evident through liver biopsy.

In treating hepatitis C infection or symptoms of hepatitis C infection, it is meant that there is either a reduction of viral titer (including complete eradication of the presence of HCV) and/or a reduction or eradication of the symptoms of hepatitis C infection. The term "reduction" as it relates to the treatment of symptoms means that there has been a reduction in the extent of the symptoms of hepatitis C. In general, such a reduction is demonstrated by objective indicators, well known to those skilled in the art. For example, comparison of liver biopsy samples taken before and after administration of a pharmaceutical composition of the present invention may indicate a reduction in fibrosis. In addition, reduction of symptoms may also be demonstrated by subjective indicators, such as a reduction in abdominal pain.

A preferred method of treating hepatitis C infection or symptoms of hepatitis C infection comprises administering to an infected individual an effective amount of a compound(s) of the present invention or a pharmaceutical composition comprising a compound(s) of the present invention. The term "effective amount" refers to an amount of the pharmaceutical composition that successfully either prevents or reduces the severity of hepatitis C symptoms or either prevents or reduces the amount of HCV in the mammal (known as viral titer). An effective amount and dosing of the compounds of the present invention is dependent on the severity and responsiveness of the hepatitis C infection, and also may depend on a number of factors, including the age and immune status of the mammal to be treated. Often the course of treatment will last several days to several months until a reduction in viral titer is effected or a diminution of disease state (symptoms) is achieved. Viral titer is routinely measured by Western blot, ELISA, RTPCR, or RNA (Northern) blot, for example.

Optimal dosing schedules are easily calculated from measurements of drug accumulation in the body. Persons of ordinary skill can easily determine optimum dosages, dosing methodologies and repetition rates. Therapeutically or prophylactically effective amounts (dosages) may vary depending on the relative potency of individual compositions, and can generally be routinely calculated based on molecular weight and EC50s in in vitro and/or animal studies. For example, given the molecular weight of the drug compound in the pharmaceutical composition and an experimentally derived effective dose such as an $IC_{50}$, for example, a dose in mg/kg may be routinely calculated.

A preferred dose range using the pharmaceutical compositions of the present invention is about 0.01 to 100 mg/kg or more preferably at a dose range of 0.1 to 10 mg/kg. The method of the present invention contemplates administering the pharmaceutical compositions from one to six times a day, and more usually one to four times a day.

EXAMPLES

Example 1

Screening of Compounds for Their Ability to Inhibit NS5B Activity

The compounds were screened for the ability to inhibit the activity of NS5B (inhibit its polymerase ability) by combining a mixture of NS5B, heteropolymeric RNA, and a test compound. Without an inhibitory test compound, the NS5B has the ability to use the heteropolymeric RNA as a template, and incorporates the radioactive nucleotides into a negative strand RNA copy. The radioactive product (the negative strand RNA) is captured on a filter, unincorporated nucleotides are removed, and the amount of radioactivity is quantitated to determine the polymerase activity. If the test compound inhibits NS5B activity, the polymerase produces either no negative strand RNA copy or a reduced amount of negative strand RNA. Thus, after removal of unincorporated nucleotides, there is no or less RNA product on the filter than present with a positive control.

For a positive control, NS5B from the BK strain (1b subtype) was expressed in *E. coli* as a protein in which the 21 C-terminal amino acids are replaced with a short linker and a hexahistidine tag (GSHHHHHH) to allow for purification. The purified protein was then mixed with radioactive nucleotides and allowed to replicate a heteropolymeric RNA substrate, which was primed by an endogenous short hairpin, resulting in an approximately 760 nucleotide product. The radioactive product was captured on a filter and quantitated after removal of the unincorporated nucleotides.

The same assay was then run in the presence of the test compounds to determine their affect on the ability of the polymerase, NS5B, to replicate a heteropolymeric RNA substrate. The reagents used in the assay are listed in Table 1.

TABLE 1

Reagents used in assay 10 mM UTP (Promega #p116B) (diluted 1:100 to 100 μM)
10 mM ATP (Promega #p113B) (diluted 1:100 to 100 μM)
10 mM CTP (Promega #p114B) (diluted 1:1000 to 10 μM)
10 mM GTP (Promega #p115B) (diluted 1:1000 to 10 μM)
BSA 10 mg/ml NEB (100X at 10 mg/ml) #007-BSA
Rnasein (Promega #N251X) 40 μ/μl
$^{33}$P-GTP (NEN-easytides NEG/606H 3000 Ci/mmol, 370 MBq/ml, 10 mCi/ml)
Falcon polypropylene 96 well plates (Becton Dickinson #351190)

TABLE 1-continued

Reagents used in assay

Millipore Multiscreen assay system-96 well-filtration plate #MADE NOB 50
Optiphase Supermix (Wallac) formulated by Fisher
Millipore Multiscreen liner for use in microbeta 1450-106 cassette (Wallac)Perkin Elmer #1450-433
1 M HEPES, pH 7.3
Amersham Pharmacia Biotech (US 16924-500 ml)
1 M $MgCl_2$ (SIGMA #M1028)
DTT (solid) (SIGMA #D9779)
RNAse free water (GIBCO-BRL #10977-023)
Dimethyl sulfoxide (Aldrich #27685-5)
Basilen Blue (Sigma, B5520)
0.5 M EDTA, pH 8 (GIBCO-BRL #15575-020)
Dibasic sodium phosphate 7 hydrate ($Na_2HPO_4.7H_2O$; Baker#3824-07)
Phosphoric acid (Baker, #0262.02)

The test compounds were tested at a concentration of 10 μg/ml in 15% DMSO. 20 μl enzyme mix was added into each well of an assay plate. The test compounds and the enzyme mix was incubated at room temperature for 15 minutes. The enzyme mix is set out at Table 2.

TABLE 2

Enzyme Mix

| Stock | Final Conc. (in 50 μl assay volume) | Per 20 μl mix (1 reaction) | Per 600 reactions |
|---|---|---|---|
| DEPC $H_2O$ | | 17.06 μl | 10236 μl |
| 1 M HEPES, pH 7.5 | 20 mM | 0.5 μl | 300 μl |
| 1 M $MgCl_2$ | 5 mM | 0.25 μl | 150 μl |
| 100 mM DTT | 1 mm | 0.5 μl | 300 μl |
| 100 μM UTP | 0.5 μM | 0.25 μl | 150 μl |
| 100 μM ATP | 1 μM | 0.5 μl | 300 μl |
| 10 μM CTP | 0.08 μM | 0.4 μl | 240 μl |
| 10 μM GTP | 0.025 μM | 0.125 μl | 75 μl |
| BSA, 10 mg/ml | 0.05 mg/ml | 0.25 μl | 150 μl |
| HCV RdRp NS5B d21BK (500 μg/ml or ~7.5 μM) | 24 nM | 0.16 μl | 96 μl |
| Total: | | 20 μl | 12 ml |

20 μl of an RNA solution and reagents set out at Table 4, were added per reaction (i.e. 20 ng of pOF per reaction or ~3 nM). The RNA solution was prepared as follows. A tube of RNA (5 ug/tube stored in 75% ethanol and 0.3 M sodium acetate) was spun down in a microcentrifuge for 20 minutes at 4° C. The ethanol was removed from the tube by inverting the tube. The RNA in the tube was then dried under a vacuum. The RNA was resuspended in 1 ml of DEPC water and placed on ice for ~60 min and gently vortexed to aid in the dissolution. The RNA was then spun briefly to ensure that all RNA solution was down to the bottom of the tube before opening cap. The RNA solution was gently transferred into a 5 ml or larger tube. Add another 3 ml of DEPC water to bring the total volume to 4 ml.

TABLE 4

Reagents

| Stock | Final concentration | Per 20 μl mix (1 reaction) | Per 600 reactions |
|---|---|---|---|
| RNAse-free water | | 2.98 μl | 1788 μl |
| Hepes, 1 M | 20 mM | 0.5 μl | 300 μl |

TABLE 4-continued

| Stock | Final concentration | Per 20 µl mix (1 reaction) | Per 600 reactions |
|---|---|---|---|
| RNase Inhibitor (40 µ/µl) | 0.4 µ/µl | 0.5 µl | 300 µl |
| $^{33}$P-GTP 3000 Ci/ mmol, 10 µCi/µl (3.3 µM) | 0.025 µM | 0.0125 µl | 7.5 µl |
| pOF | 3 nM | 16 µl | 9600 µl |

The reaction was allowed to incubate reaction at room temperature (22-25°C) for 2 hours. The reaction was stopped by adding 50 µl of 170 mM EDTA (for a final EDTA concentration of 85 mM).

Filters of a Millipore multiscreen assay plate were prewetted by adding 200 µl of 0.5 M sodium phosphate buffer, pH 7.0, into each well and allowed to stand at room temperature for two to three minutes.

The multiscreen filter plate was placed onto a Millipore Manifold and a vacuum turned on to allow buffer to flow through. The vacuum was then turned off. 80 µl of the reaction product was transferred into each well of the filter plate and allowed to stand for two to three minutes. The vacuum was then turned on to filter the reaction product. Again, the vacuum was turned off and 200 µl of 0.5 M sodium phosphate buffer, pH 7.0, into each well to wash filter was added. The vacuum was then turned on to remove the wash. This wash step was repeated three more times.

The polypropylene bottom was removed from the assay plate. The filter was spot dried at the bottom with a paper towel and then allowed to air dry on a bench for 1 hour. 40 µl Super Mix scintillant was added to the plate. The top of the plate was sealed with tape and placed into a either a Packard carrier or micro-beta carrier.

The plate was counted using a Packard Topcount or micro-beta counter. Program 10 for $^{33}$P in Top count or $^{33}$P program in micro-beta was used.

The percent inhibition was calculated after background subtraction as a percent reduction of activity relative to the positive control (average value of the plate excluding the negative controls). For the primary screen hits were chosen as showing >75% inhibition.

The results of the assays for some of the preferred compounds of the present invention are presented below in table 5.

TABLE 5

| Compound | IC$_{50}$ |
|---|---|
| 2-{[(2,4-dichlorophenoxy)acetyl]amino}benzoic acid | 0.45 |
| 2-{[(2,5-dimethylphenoxy)acetyl]amino}benzoic acid | 1.36 |
| 2-{[(2-ethoxy-5-Z-(2-propenyl)phenoxy)acetyl]amino}benzoic acid | 4.24 |
| 2-{[(2-bromo-5-fluorophenoxy)acetyl]amino}benzoic acid | 3.27 |
| 2-{[(2-methyl-5-nitrophenoxy)acetyl]amino}benzoic acid | 4.09 |
| 2-{[(2-fluoro-5-methylphenoxy)acetyl]amino}benzoic acid | 2.47 |
| 2-[2-(4-Bromo-phenoxy)-acetylamino]-benzoic acid | 3.23 |
| 2-[2-(3-Bromo-phenoxy)-acetylamino]-benzoic acid | 1.14 |
| 2-[2-(2-Bromo-phenoxy)-acetylamino]-benzoic acid | 0.99 |
| 2-[2-(4-Bromo-phenoxy)-propionylamino]-benzoic acid | 1.60 |
| 2-[2-(4-Bromo-phenylsulfanyl)-acetylamino]-benzoic acid | 4.37 |
| 2-[2-(4-Chloro-phenoxy)-acetylamino]-benzoic acid | 1.64 |
| 2-[2-(4-Fluoro-phenoxy)-acetylamino]-benzoic acid | 2.25 |
| 2-{[(3-chlorophenoxy)acetyl]amino}benzoic acid | 2.58 |
| 2-{[(3-chlorophenoxy)acetyl]amino}-5-fluorobenzoic acid | 1.47 |
| 2-{[(3-chlorophenoxy)acetyl]amino}-5-hydroxybenzoic acid | 0.26 |
| 2-{[(3,4-dimethylphenoxy)acetyl]amino}-5-hydroxybenzoic acid | 0.36 |
| 2-{[(3-bromophenoxy)acetyl]amino}-5-hydroxybenzoic acid | 0.15 |
| 2-{[(2S)-2-(4-chlorophenoxy)propanoyl]amino}benzoic acid | 0.76 |
| 2-{[(2,3-dichlorophenoxy)acetyl]amino}-5-hydroxybenzoic acid | 0.24 |
| 2-{[(2,4,5-trichlorophenoxy)acetyl]amino}benzoic acid, | 0.03 |
| 2-{[(2,4-dibromophenoxy)acetyl]amino}benzoic acid | 0.63 |
| 2-{[(2-chlorophenoxy)acetyl]amino}benzoic acid | 4.30 |
| 2-{[N-(3-bromophenyl)glycyl]amino}benzoic acid | 0.87 |
| 2-{[N-(4-bromo-3-chlorophenyl)-N-methylglycyl]amino}benzoic acid | 4.49 |
| 2-{[(4-chloro-2-methylphenoxy)acetyl]amino}benzoic acid | 0.57 |
| 2-{[(5-chloro-2-methylphenoxy)acetyl]amino}benzoic acid | 0.44 |
| 2-{[(3,4-difluorophenoxy)acetyl]amino}benzoic acid | 1.60 |
| 2-(4-chlorophenoxy)-N-[2-(1H-tetrazol-5-yl)phenyl]acetamide | 2.29 |
| 2-{[N-(3,4-dibromophenyl)-N-methylglycyl]amino}benzoic acid | 0.14 |
| 2-{[N-(2,5-dibromophenyl)glycyl]amino}benzoic acid | 0.14 |
| 2-{[N-(2,5-dibromophenyl)glycyl]amino}benzoic acid | 0.18 |
| 2-{[(2-cyanophenoxy)acetyl]amino}benzoic acid | 4.20 |
| 5-hydroxy-2-{[(2,4,5-trichlorophenoxy)acetyl]amino}benzoic acid | 0.01 |
| 2-{[(2-chloro-4,5-dimethylphenoxy)acetyl]amino}benzoic acid | 0.73 |
| 2-({[4-chloro-3-(trifluoromethyl)phenyl]acetyl}amino)benzoic acid | 1.98 |
| 2-{[(2-bromo-4-chloro-5-methylphenoxy)acetyl]amino}benzoic acid | 0.11 |
| 2-{[(2-ethyl-4,5-dimethylphenoxy)acetyl]amino}benzoic acid | 4.34 |
| 2-({[(3,4-dichlorophenyl)sulfanyl]acetyl}amino)benzoic acid | 1.64 |
| 2-({[(4-chlorophenyl)sulfanyl]acetyl}amino)benzoic acid | 4.41 |
| 2-{[(2-bromo-4,5-difluorophenoxy)acetyl]amino}benzoic acid | 0.94 |
| 2-({[3-(trifluoromethyl)phenoxy]acetyl}amino)benzoic acid | 2.01 |
| 2-{[(2-bromo-4-chloro-5-methylphenoxy)acetyl]amino}-5-hydroxybenzoic acid | 0.02 |
| 2-{[(2,4,5-trifluorophenoxy)acetyl]amino}benzoic acid | 1.27 |
| 2-{[(3,5-dichlorophenoxy)acetyl]amino}-5-hydroxybenzoic acid | 0.34 |
| 2-({[(2,4,5-trichlorophenyl)thio]acetyl}amino)benzoic acid | 0.32 |
| 2-{[N-(3,4-dichlorophenyl)-N-methylglycyl]amino}benzoic acid | 0.17 |
| 2-{[(3,5-difluorophenoxy)acetyl]amino}benzoic acid | 3.93 |
| 2-{[(3,5-difluorophenoxy)acetyl]amino}-5-hydroxybenzoic acid | 0.62 |
| 2-{[(2-bromophenoxy)acetyl]amino}-5-hydroxybenzoic acid | 0.60 |
| 2-{[(2-chloro-6-methylphenoxy)acetyl]amino}benzoic acid | 0.05 |
| 2-{[(4-chloro-3-ethylphenoxy)acetyl]amino}benzoic acid | 0.41 |
| 2-{[N-(2,4,5-trichlorophenyl)glycyl]amino}benzoic acid | 0.05 |
| 5-hydroxy-2-{[N-(2,4,5-tichlorophenyl)glycyl]amino}benzoic acid | 0.05 |
| 2-{[(3-chloro-4-methylphenoxy)acetyl]amino}benzoic acid | 1.18 |
| 2-{[(3-chloro-4-methylphenoxy)acetyl]amino}-5-hydroxybenzoic acid | 0.23 |
| 2-{[(2-chloro-5-fluorophenoxy)acetyl]amino}benzoic acid | 2.32 |
| 2-{[(2-chloro-5-fluorophenoxy)acetyl]amino}-5-hydroxybenzoic acid | 0.96 |
| 2-{[(3-chloro-4-fluorophenoxy)acetyl]amino}benzoic acid | 0.39 |
| 2-{[(3-chloro-4-fluorophenoxy)acetyl]amino}-5-hydroxybenzoic acid | 0.05 |
| 2-{[(4-chloro-3-fluorophenoxy)acetyl]amino}benzoic acid | 1.19 |
| 2-{[N-(3,4-difluorophenyl)glycyl]amino}benzoic acid | 1.84 |
| 2-{[N-(3,4-dichlorophenyl)glycyl]amino}benzoic acid | 0.20 |
| 2-{[N-(2,5-dichlorophenyl)glycyl]amino}-5-hydroxybenzoic acid | 0.04 |
| 2-{[N-(4-chloro-2-fluorophenyl)glycyl]amino}benzoic acid | 0.72 |
| 2-{[(4-chloro-3-fluorophenoxy)acetyl]amino}-5-hydroxybenzoic acid | 0.35 |
| 2-{[N-(2-fluoro-4-methylphenyl)glycyl]amino}benzoic acid | 3.22 |
| 2-{[N-(3,4-dichlorophenyl)glycyl]amino}-5-hydroxybenzoic acid | 0.03 |
| 2-{[N-(2,5-dichlorophenyl)glycyl]amino}benzoic acid | 0.37 |
| 2-{[N-(2,5-dichlorophenyl)glycyl]amino}-5-hydroxybenzoic acid | 0.20 |
| 2-{[N-(3,4-dichlorophenyl)-N-ethylglycyl]amino}benzoic acid | 1.55 |
| 2-{[N-(3,4-dichlorophenyl)-N-ethylglycyl]amino}-5-hydroxybenzoic acid | 0.39 |
| 2-{[N-(3,4-dichlorophenyl)-N-propylglycyl]amino}benzoic acid | 1.58 |
| 2-{[N-(3,4-dichlorophenyl)-N-propylglycyl]amino}-5-hydroxybenzoic acid | 0.38 |
| 2-{[N-(2,5-dichlorophenyl)-N-methylglycyl]amino}-5-hydroxybenzoic acid | 1.52 |
| 2-{[N-(3,4-dichlorophenyl)-N-methylglycyl]amino}-5-hydroxybenzoic acid | 0.02 |
| 2-{[N-(3-chloro-4-fluorophenyl)glycyl]amino}benzoic acid | 0.21 |

We claim:

1. A method of treating hepatitis C in a mammal having symptoms of hepatitis C comprising administering to said mammal an effective amount of a pharmaceutical composition comprising a compound having the structure

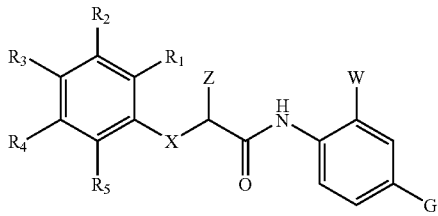

and pharmaceutically acceptable salts thereof, wherein:
$R_1$, $R_2$, $R_3$, $R_4$ and $R_5$ are independently selected from the group consisting of hydrogen, halogen, methyl, ethyl, methoxy, nitro, $C_2$-$C_4$ alkenyl, cyano, and trifluoromethyl;
X is O, S, NH, or NR where R is a $C_1$-$C_4$ alkyl group;
W is $CO_2H$ or 5-tetrazolyl;
Z is hydrogen or mono-methyl and
G is either OH, F, or hydrogen.

2. The method of claim 1 wherein the compound is selected from the group consisting of
2-{[(2,4-dichlorophenoxy)acetyl]amino}benzoic acid;
2-{[(2,5-dimethylphenoxy)acetyl]amino}benzoic acid;
2-{[(2-ethoxy-5-Z-(2-propenyl)phenoxy)acetyl]amino}benzoic acid;
2-{[(2-bromo-5-fluorophenoxy)acetyl]amino}benzoic acid;
2-{[(2-methyl-5-nitrophenoxy)acetyl]amino}benzoic acid;
2-{[(2-fluoro-5-methylphenoxy)acetyl]amino}benzoic acid;
2-[2-(4-Bromo-phenoxy)-acetylamino]-benzoic acid;
2-[2-(3-Bromo-phenoxy)-acetylamino]-benzoic acid;
2-[2-(2-Bromo-phenoxy)-acetylamino]-benzoic acid;
2-[2-(4-Bromo-phenoxy)-propionylamino]-benzoic acid;
2-[2-(4-Bromo-phenylsulfanyl)-acetylamino]-benzoic acid;
2-[2-(4-Chloro-phenoxy)-acetylamino]-benzoic acid;
2-[2-(4-Fluoro-phenoxy)-acetylamino]-benzoic acid;
2-{[(3-chlorophenoxy)acetyl]amino}benzoic acid;
2-{[(3-chlorophenoxy)acetyl]amino}-5-fluorobenzoic acid;
2-{[(3-chlorophenoxy)acetyl]amino}-5-hydroxybenzoic acid;
2-{[(3,4-dimethylphenoxy)acetyl]amino}-5-hydroxybenzoic acid;
2-{[(3-bromophenoxy)acetyl]amino}-5-hydroxybenzoic acid;
2-{[(2S)-2-(4-chlorophenoxy)propanoyl]amino}benzoic acid;
2-{[(2,3-dichlorophenoxy)acetyl]amino}-5-hydroxybenzoic acid;
2-{[(2,4,5-trichlorophenoxy)acetyl]amino}benzoic acid;
2-{[(2,4-dibromophenoxy)acetyl]amino}benzoic acid;
2-{[(2-chlorophenoxy)acetyl]amino}benzoic acid;
2-{[N-(3-bromophenyl)glycyl]amino}benzoic acid;
2-{[N-(4-bromo-3-chlorophenyl)-N-methylglycyl]amino}benzoic acid;
2-{[(4-chloro-2-methylphenoxy)acetyl]amino}benzoic acid;
2-{[(5-chloro-2-methylphenoxy)acetyl]amino}benzoic acid;
2-{[(3,4-difluorophenoxy)acetyl]amino}benzoic acid;
2-(4-chlorophenoxy)-N-[2-(1H-tetrazol-5-yl)phenyl]acetamide;
2-{[N-(3,4-dibromophenyl)-N-methylglycyl]amino}benzoic acid;
2-{[N-(2,5-dibromophenyl)glycyl]amino}benzoic acid;
2-{[(2-cyanophenoxy)acetyl]amino}benzoic acid;
5-hydroxy-2-{[(2,4,5-trichlorophenoxy)acetyl]amino}benzoic acid;
2-{[(2-chloro-4,5-dimethylphenoxy)acetyl]amino}benzoic acid;
2-({[4-chloro-3-(trifluoromethyl)phenoxy]acetyl}amino)benzoic acid;
2-{[(2-bromo-4-chloro-5-methylphenoxy)acetyl]amino)benzoic acid;
2-{[(2-ethyl-4,5-dimethylphenoxy)acetyl]amino}benzoic acid;
2-({[(3,4-dichlorophenyl)sulfanyl]acetyl}amino)benzoic acid;
2-({[(4-chlorophenyl)sulfanyl]acetyl}amino)benzoic acid;
2-{[(2-bromo-4,5-difluorophenoxy)acetyl]amino}benzoic acid;
2-({[3-(trifluoromethyl)phenoxy]acetyl}amino)benzoic acid;
2-{[(2-bromo-4-chloro-5-methylphenoxy)acetyl]amino}-5-hydroxybenzoic acid;
2-{[(2,4,5-trifluorophenoxy)acetyl]amino}benzoic acid;
2-{[(3,5-dichlorophenoxy)acetyl]amino}-5-hydroxybenzoic acid;
2-({[(2,4,5-trichlorophenyl)thio]acetyl}amino)benzoic acid;
2-{[N-(3,4-dichlorophenyl)-N-methylglycyl]amino}benzoic acid;
2-{[(3,5-difluorophenoxy)acetyl]amino}benzoic acid;
2-{[(3,5-difluorophenoxy)acetyl]amino}-5-hydroxybenzoic acid;
2-{[(2-bromophenoxy)acetyl]amino}-5-hydroxybenzoic acid;
2-{[(2-chloro-6-methylphenoxy)acetyl]amino}benzoic acid;
2-{[(4-chloro-3-ethylphenoxy)acetyl]amino}benzoic acid;
2-{[N-(2,4,5-trichlorophenyl)glycyl]amino}benzoic acid;
5-hydroxy-2-{[N-(2,4,5-trichlorophenyl)glycyl]amino}benzoic acid;
2-{[(3-chloro-4-methylphenoxy)acetyl]amino}benzoic acid
2-{[(3-chloro-4-methylphenoxy)acetyl]amino}-5-hydroxybenzoic acid;
2-{[(2-chloro-5-fluorophenoxy)acetyl]amino}benzoic acid;
2-{[(2-chloro-5-fluorophenoxy)acetyl]amino}-5-hydroxybenzoic acid;
2-{[(3-chloro-4-fluorophenoxy)acetyl]amino}benzoic acid;
2-{[(3-chloro-4-fluorophenoxy)acetyl]amino}-5-hydroxybenzoic acid;
2-{[(4-chloro-3-fluorophenoxy)acetyl]amino}benzoic acid;
2-{[N-(3,4-difluorophenyl)glycyl]amino}benzoic acid;
2-{[N-(3,4-dichlorophenyl)glycyl]amino}benzoic acid;
2-{[N-(2,5-dibromophenyl)glycyl]amino}-5-hydroxybenzoic acid;
2-{[N-(4-chloro-2-fluorophenyl)glycyl]amino}benzoic acid;
2-{[(4-chloro-3-fluorophenoxy)acetyl]amino}-5-hydroxybenzoic acid;
2-{[N-(2-fluoro-4-methylphenyl)glycyl]amino}benzoic acid;

2-{[N-(3,4-dichlorophenyl)glycyl]amino}-5-hydroxybenzoic acid;
2-{[N-(2,5-dichlorophenyl)glycyl]amino}benzoic acid;
2-{[N-(2,5-dichlorophenyl)glycyl]amino}-5-hydroxybenzoic acid;
2-{[N-(3,4-dichlorophenyl)-N-ethylglycyl]amino}benzoic acid;
2-{[N-(3,4-dichlorophenyl)-N-ethylglycyl]amino}-5-hydroxybenzoic acid;
2-{[N-(3,4-dichlorophenyl)-N-propylglycyl]amino}benzoic acid;
2-{[N-(3,4-dichlorophenyl)-N-propylglycyl]amino}-5-hydroxybenzoic acid;
2-{[N-(2,5-dichlorophenyl)-N-methylglycyl]amino}-5-hydroxybenzoic acid;
2-{[N-(3,4-dichlorophenyl)-N-methylglycyl]amino}-5-hydroxybenzoic acid;
2-{[N-(3-chloro-4-fluorophenyl)glycyl]amino}benzoic acid;
2-{[(3,4,-dimethylphenoxy)acetyl]amino}-5-hydroxybenzoic acid;
2-{[(2-chlorophenoxy)acetyl]amino}-5-hydroxybenzoic acid;
2-{[(2-bromo-4-methylphenoxy)acetyl]amino}benzoic acid;
2-{[(4-nitrophenoxy)acetyl]amino}-5-hydroxybenzoic acid;
2-{[2-(2-chloro-phenoxy)acetyl]amino}benzoic acid;
2-[{(4-bromophenyl)methyl}{2-isopropyl-5-methylphenoxyacetyl}amino]benzoic acid;
2-{[(4-cyclohexylphenoxy)acetyl]amino}benzoic acid; and pharmaceutically acceptable salts thereof.

3. The method of claim 1 wherein the compound is selected from the group consisting of
2-{[(2,4,5-trichlorophenoxy)acetyl]amino}benzoic acid;
2-{[N-(2,5-dibromophenyl)glycyl]amino}-5-hydroxybenzoic acid;
2-{[N-(3,4-dichlorophenyl)glycyl]amino}-5-hydroxybenzoic acid; and pharmaceutically acceptable salts thereof.

4. The method of claim 1 wherein the compound is selected from the group consisting of
5-hydroxy-2-{[(2,4,5-trichlorophenoxy)acetyl]amino}benzoic acid;
2-{[(2-bromo-4-chloro-5-methylphenoxy)acetyl]amino}-5-hydroxybenzoic acid;
2-{[N-(3,4-dichlorophenyl)-N-methylglycyl]amino}-5-hydroxybenzoic acid; and pharmaceutically acceptable salts thereof.

5. The method of claim 1 wherein the mammal is human.

6. The method of claim 5 wherein the composition is administered orally to said human.

7. The method of claim 6 wherein the compound is administered orally at a dose range of about 0.01 to 100 mg/kg from 1 to 6 times a day.

8. The method of claim 7 wherein the compound is administered orally at a dose range of about 0.1 to 10 mg/kg from 1 to 6 times a day.

9. The method of claim 8 wherein the compound is administered from 1 to 4 times a day.

10. The method of claim 5 wherein the composition is administered subcutaneously to said human.

11. A method of treating hepatitis C in a mammal having symptoms of hepatitis C comprising administering to said mammal an effective amount of a pharmaceutical composition comprising a compound having the structure

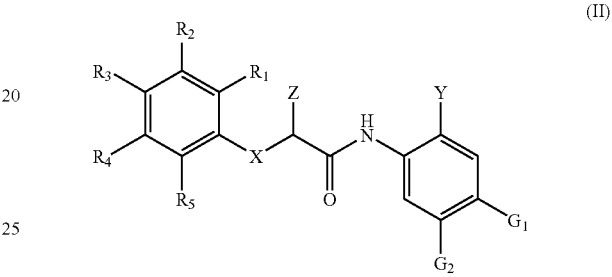

(II)

and pharmaceutically acceptable salts thereof, wherein:
$R_1$, $R_2$, $R_3$, $R_4$ and $R_5$ are independently selected from the group consisting of hydrogen, halogen, methyl, ethyl, methoxy, nitro, $C_2$-$C_4$ alkenyl, cyano, and trifluoromethyl;
X is O, S, NH, or NR where R is a $C_1$-$C_4$ alkyl group;
Y is $CO_2H$ or $CO_2CH_3$;
Z is hydrogen or mono-methyl;
$G_1$ is OH, F, methoxy or hydrogen; and
$G_2$ is either OH, Cl, methoxy or hydrogen.

12. The method of claim 11 wherein the compound is selected from the group consisting of
2-[(4-chlorophenoxy)acetylamino]-benzoic acid methyl ester;
2-[(4-methoxyphenoxy)acetylamino]-benzoic acid methyl ester;
2-[(4-cyclohexylphenoxy)acetylamino]-4,5-dimethoxybenzoic acid;
2-[(2-phenoxy)propionylamino]-4-hydroxybenzoic acid;
2-{[(3,4,-dimethylphenoxy)acetyl]amino}-4-hydroxybenzoic acid;
2-[(3-methylphenoxy)acetylamino]-4,5-dimethoxybenzoic acid;
2-[(3-methylphenoxy)acetylamino]-4-chlorobenzoic acid; and pharmaceutically acceptable salts thereof.

* * * * *